(12) United States Patent
Hamer et al.

(10) Patent No.: US 9,622,886 B2
(45) Date of Patent: Apr. 18, 2017

(54) SIDE BRANCHED ENDOLUMINAL PROSTHESES AND METHODS OF DELIVERY THEREOF

(71) Applicant: W. L. Gore & Associates, Inc., Newark, DE (US)

(72) Inventors: Rochelle M. Hamer, Flagstaff, AZ (US); Eric Gerard Johnson, New Albany, IN (US)

(73) Assignee: W. L. Gore & Associates, Inc., Newark, DE (US)

( * ) Notice: Subject to any disclaimer, the term of this patent is extended or adjusted under 35 U.S.C. 154(b) by 400 days.

(21) Appl. No.: 14/034,368

(22) Filed: Sep. 23, 2013

(65) Prior Publication Data

US 2014/0025162 A1    Jan. 23, 2014

Related U.S. Application Data

(63) Continuation of application No. 13/562,200, filed on Jul. 30, 2012, which is a continuation of application (Continued)

(51) Int. Cl.
*A61F 2/07* (2013.01)
*A61F 2/856* (2013.01)
(Continued)

(52) U.S. Cl.
CPC ............... *A61F 2/856* (2013.01); *A61F 2/07* (2013.01); *A61F 2/958* (2013.01); *A61F 2/966* (2013.01); *A61F 2/95* (2013.01); *A61F 2/954* (2013.01); *A61F 2/962* (2013.01); *A61F 2/97* (2013.01); *A61F 2002/061* (2013.01);
(Continued)

(58) Field of Classification Search
CPC .............................................. A61F 2/962–2/97
See application file for complete search history.

(56) References Cited

U.S. PATENT DOCUMENTS

| 5,273,052 A | 12/1993 | Kraus et al. |
| 5,755,769 A | 5/1998 | Richard et al. |

(Continued)

FOREIGN PATENT DOCUMENTS

| EP | 1 512 380 | 3/2005 |
| WO | WO-9827894 A1 | 7/1998 |

(Continued)

*Primary Examiner* — Yashita Sharma
*Assistant Examiner* — Rebecca Preston

(57) ABSTRACT

An expandable prosthetic device and method of delivery that allows the initial placement of multiple guidewires into selected target sites. The prosthesis includes a main body device. This main body device has a separate side branch guidewire lumen that passes through the main body device and through a side opening in the main body device. As the main body device is advanced, the side opening is self guided (by the side branch guidewire) and self-aligns to the side branch vessel ostium. The main body device is then deployed, leaving the side branch guidewire in place. A side branch device is then advanced along the side branch guidewire through the main body device, through the side wall opening and into the native side branch vessel. The side branch device can then be deployed to engage the main body device and the native side branch vessel.

10 Claims, 14 Drawing Sheets

Related U.S. Application Data

No. 11/739,136, filed on Apr. 24, 2007, now Pat. No. 8,273,115.

(51) Int. Cl.

| | |
|---|---|
| *A61F 2/958* | (2013.01) |
| *A61F 2/966* | (2013.01) |
| *A61F 2/95* | (2013.01) |
| *A61F 2/962* | (2013.01) |
| *A61F 2/97* | (2013.01) |
| *A61F 2/954* | (2013.01) |
| *A61F 2/82* | (2013.01) |
| *A61F 2/06* | (2013.01) |

(52) U.S. Cl.
CPC ... *A61F 2002/075* (2013.01); *A61F 2002/826* (2013.01); *A61F 2002/9511* (2013.01); *A61F 2002/9522* (2013.01); *A61F 2210/0004* (2013.01); *A61F 2210/0014* (2013.01); *A61F 2230/0006* (2013.01); *A61F 2250/006* (2013.01)

(56) References Cited

U.S. PATENT DOCUMENTS

| | | | |
|---|---|---|---|
| 6,042,605 | A | 3/2000 | Martin et al. |
| 6,224,627 | B1 | 5/2001 | Armstrong |
| 6,264,682 | B1 | 7/2001 | Wilson et al. |
| 6,338,724 | B1 | 1/2002 | Dossa |
| 6,352,561 | B1 | 3/2002 | Leopold et al. |
| 6,361,544 | B1 | 3/2002 | Wilson et al. |
| 6,361,637 | B2 | 3/2002 | Martin et al. |
| 6,520,986 | B2 | 2/2003 | Martin et al. |
| 6,520,988 | B1 | 2/2003 | Colombo et al. |
| 6,551,350 | B1 | 4/2003 | Thornton et al. |
| 6,599,316 | B2 | 7/2003 | Vardi et al. |
| 6,645,242 | B1 | 11/2003 | Quinn |
| 6,682,556 | B1 | 1/2004 | Ischinger |
| 6,890,349 | B2 | 5/2005 | McGuckin et al. |
| 6,908,477 | B2 | 6/2005 | McGuckin et al. |
| 6,962,602 | B2 | 11/2005 | Vardi et al. |
| 7,537,606 | B2 | 5/2009 | Hartley et al. |
| 2002/0029077 | A1* | 3/2002 | Leopold ............ A61F 2/07 623/1.11 |
| 2002/0072790 | A1* | 6/2002 | McGuckin, Jr. ......... A61F 2/07 623/1.12 |
| 2002/0173835 | A1 | 11/2002 | Bourang et al. |
| 2003/0055483 | A1 | 3/2003 | Gumm |
| 2003/0167083 | A1 | 9/2003 | Lashinski et al. |
| 2003/0236566 | A1 | 12/2003 | Heuser |
| 2004/0098081 | A1 | 5/2004 | Landreville et al. |
| 2004/0102719 | A1 | 5/2004 | Keith et al. |
| 2004/0133130 | A1 | 7/2004 | Ferry et al. |
| 2004/0153136 | A1 | 8/2004 | Vardi et al. |
| 2004/0172121 | A1 | 9/2004 | Eidenschink et al. |
| 2004/0199073 | A1 | 10/2004 | Ma |
| 2004/0230287 | A1 | 11/2004 | Hartley et al. |
| 2005/0038494 | A1* | 2/2005 | Eidenschink ............ A61F 2/95 623/1.11 |
| 2005/0182476 | A1 | 8/2005 | Hartley et al. |
| 2005/0187602 | A1 | 8/2005 | Eidenschink |
| 2006/0004433 | A1 | 1/2006 | Greenberg et al. |
| 2006/0015171 | A1 | 1/2006 | Armstrong |
| 2006/0041303 | A1 | 2/2006 | Isreal |
| 2006/0100694 | A1 | 5/2006 | Globerman |
| 2006/0287712 | A1 | 12/2006 | Eidenschink |
| 2007/0083215 | A1 | 4/2007 | Hamer et al. |
| 2007/0106245 | A1 | 5/2007 | McQueen et al. |
| 2007/0168020 | A1 | 7/2007 | Brucker |
| 2007/0299494 | A1 | 12/2007 | Zukowski |
| 2008/0269866 | A1 | 10/2008 | Hamer et al. |
| 2008/0133802 | A1 | 11/2008 | Hamer et al. |
| 2010/0049298 | A1 | 2/2010 | Hamer et al. |
| 2012/0109279 | A1* | 5/2012 | Mayberry ............... A61F 2/07 623/1.11 |
| 2014/0025162 | A1 | 1/2014 | Hamer et al. |

FOREIGN PATENT DOCUMENTS

| | | |
|---|---|---|
| WO | 9934740 A1 | 7/1999 |
| WO | WO-9934749 A1 | 7/1999 |
| WO | WO-0033770 A2 | 6/2000 |
| WO | 0074595 A1 | 12/2000 |
| WO | 2005025458 A1 | 3/2005 |
| WO | 2007/001519 | 1/2007 |
| WO | 02/30329 | 4/2007 |

\* cited by examiner

200
SIDE BRANCHED ENDOLUMINAL PROSTHESES AND METHODS OF DELIVERY THEREOF

FIELD OF THE INVENTION

The present invention relates to endoluminal prostheses and methods of delivery thereof. The endoluminal prostheses and method of delivery are particularly suited for use in bifurcated regions of body lumens.

BACKGROUND OF THE INVENTION

Stents or stent grafts are examples of expandable endoluminal prosthetic devices which are used to maintain, open or dilate stenotic lesions in body lumens or to cover and repair an aneurysm. Vascular disease may occur at a branch or bifurcation in a vessel. Placement and deployment of these prosthetic devices at bifurcations can often be problematic. One current technique is to initially deploy across an aneurysm, a main body prosthetic device having a side wall opening. The side wall opening is aligned with the side branch ostium. A second prosthetic device is then deployed through the main body prosthetic device side wall opening and into the side branch vessel. Procedural complications are often encountered while practicing this technique. These complications typically relate to the accurate placement of the main body prosthetic device and in particular to the precise alignment of the side wall opening to the native side branch vessel. Subsequent placement of the side branch guidewire through the main body prosthetic device, through the side wall opening and then into the side branch vessel can also be problematic. The deployment of the side branch prosthetic device into the native vessel can present problems relating to the longitudinal placement of the device.

Alternate procedures for treating bifurcated vessels place the guidewires prior to the device deployments. After the main body prosthetic device is deployed, it is advantageous to then remove the main body delivery catheter prior to the delivery of the side branch prosthetic device. Typical delivery systems incorporate guidewires that are contained or captured within the delivery catheter. The catheter removal therefore requires careful management of the side branch guidewire to prevent its dislodgement during the removal of the delivery catheter.

SUMMARY OF THE INVENTION

An aspect of the invention includes an expandable prosthesis comprising:

an expandable main body device having a first open end and a second open end, a wall extending from the first open end to the second open end, a lumen extending from the first open end to the second open end, and at least one side opening in the wall; and guidewire tube having a first end, a second end and a lumen, the guidewire tube extending from at least the main body device side opening, through the main body device lumen to a point proximal to the second open end, wherein the guidewire tube is removable from the main body device while the main body device is in a compressed state.

DETAILED DESCRIPTION OF THE INVENTION

An aspect of the invention includes an expandable prosthesis comprising an expandable main body device having a first open end and a second open end, a wall extending from the first open end to the second open end, a lumen extending from the first open end to the second open end, and at least one side opening in the wall; and a guidewire tube having a first end, a second end and a lumen, the guidewire tube extending from at least the main body device side opening, through the main body device lumen to a point proximal to the second open end, wherein the guidewire tube is removable from the main body device while the main body device is in a compressed state.

A further aspect of the invention provides methods for delivery of an expandable prosthesis that overcome the drawbacks relating to conventional devices and delivery methods. The present invention allows for the initial placement of multiple guidewires into selected target sites. The guidewire placement is simplified since there are no endoluminal devices complicating the guidewire placement. As a failsafe, the procedure can be aborted if the guidewires cannot be properly placed. After proper placement of the guidewires is confirmed, a main body prosthetic device can be advanced to the treatment site. This main body device has a separate side branch guidewire that passes through the main body device and through the side opening in the main body device. Therefore as the main body device is advanced, the side opening is self guided (by the side branch guidewire) and self aligns to the side branch vessel ostium. The main body device is then deployed, leaving the side branch guidewire in place. The side branch guidewire is released as the main body device is deployed. The delivery catheter can then be readily removed without dislodging the placement of the side branch guidewire. A side branch prosthetic device can then be advanced along the side branch guidewire through the main body device, through the side wall opening and into the native side branch vessel. The side branch device can then be deployed to engage the main body device and the native side branch vessel.

In an aspect of the invention a side branch guidewire lumen is formed by a relatively short, removable tube. This tube preserves a lumen during the compaction and storage of the main body prosthetic device and can be simply removed after a guidewire is inserted prior to the advancement of the device into the body. The short length of the removable guidewire tube permits a single operator to back load and advance the device, similar to a conventional balloon catheter configured for "rapid exchange".

Figure 1:
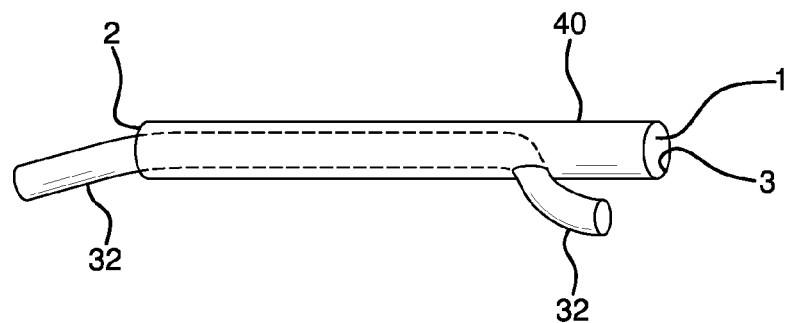
FIG. 1 is a perspective view of a prosthetic device according to an aspect of the invention.

Further understanding of the invention may be had with reference to the figures. Shown in FIG. 1 is a compressed prosthetic device according to the present invention. The expandable prosthesis comprises an expandable main body device 40 having a first open end 1 and a second open end 2, a wall extending from the first open end 1 to the second open end 2, a lumen 3 extending from the first open end 1 to the second open end 2, and at least one side opening 42 in the wall; and a guidewire tube 32 having a first end 11, a second end 12 and a lumen 13, the guidewire tube 32 extending from at least the main body device side opening 42, through the main body device lumen 3 to a point proximal to the second open end 2, wherein the guidewire tube 32 is removable from the main body device 40 while the main body device 40 is in a compressed state.

The expandable main body device can be either self-expanding or balloon expandable. Typically, a self-expanding device will include at least one shape memory material, such as nitinol. The main body device can comprise a stent or stent graft. Suitable stent materials include, in addition to nitinol, for example, metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

The main body device can comprise a stent at either the first open end, the second open end, or at both the first open end and the second open end. Moreover, the stent can be a single stent extending from the first open end to the second open end. In an aspect of the invention, graft material is used to form the wall and extends from the first open end to the second open end. Grafts can have various configurations and can be fabricated, for example, from tubes, sheets or films formed into tubular shapes, woven or knitted fibers or ribbons or combinations thereof. Graft materials can include conventional medical grade materials such as nylon, polyester, polyethylene, polypropylene, polytetrafluoroethylene, polyurethane and elastomeric organosilicon polymers.

Stents can be used alone or in combination with graft materials. Stents can be configured on the external or internal surface of a graft or may be incorporated into the internal wall structure of a graft.

Figure 2:
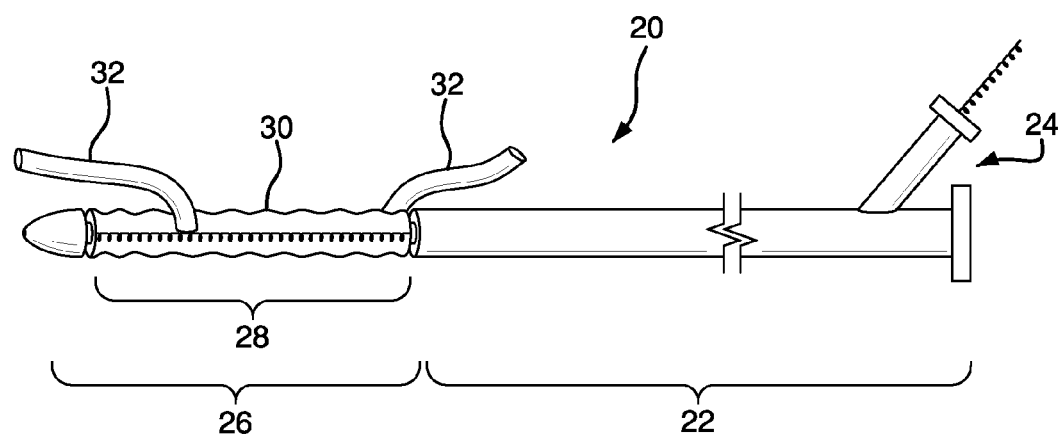
FIG. 2 is a perspective view of a catheter assembly having a removable side branch guidewire tube.

Shown in FIG. 2 is a side view of a catheter assembly 20 having a proximal catheter portion 22, a proximal hub assembly 24 and a distal catheter portion 26. The distal catheter portion 26 comprises a main body stent (or stent graft) portion 28. The main body stent is shown in a compressed state, maintained by a constraining sleeve 30. Also shown is a removable side branch guidewire tube 32.

Figure 3:
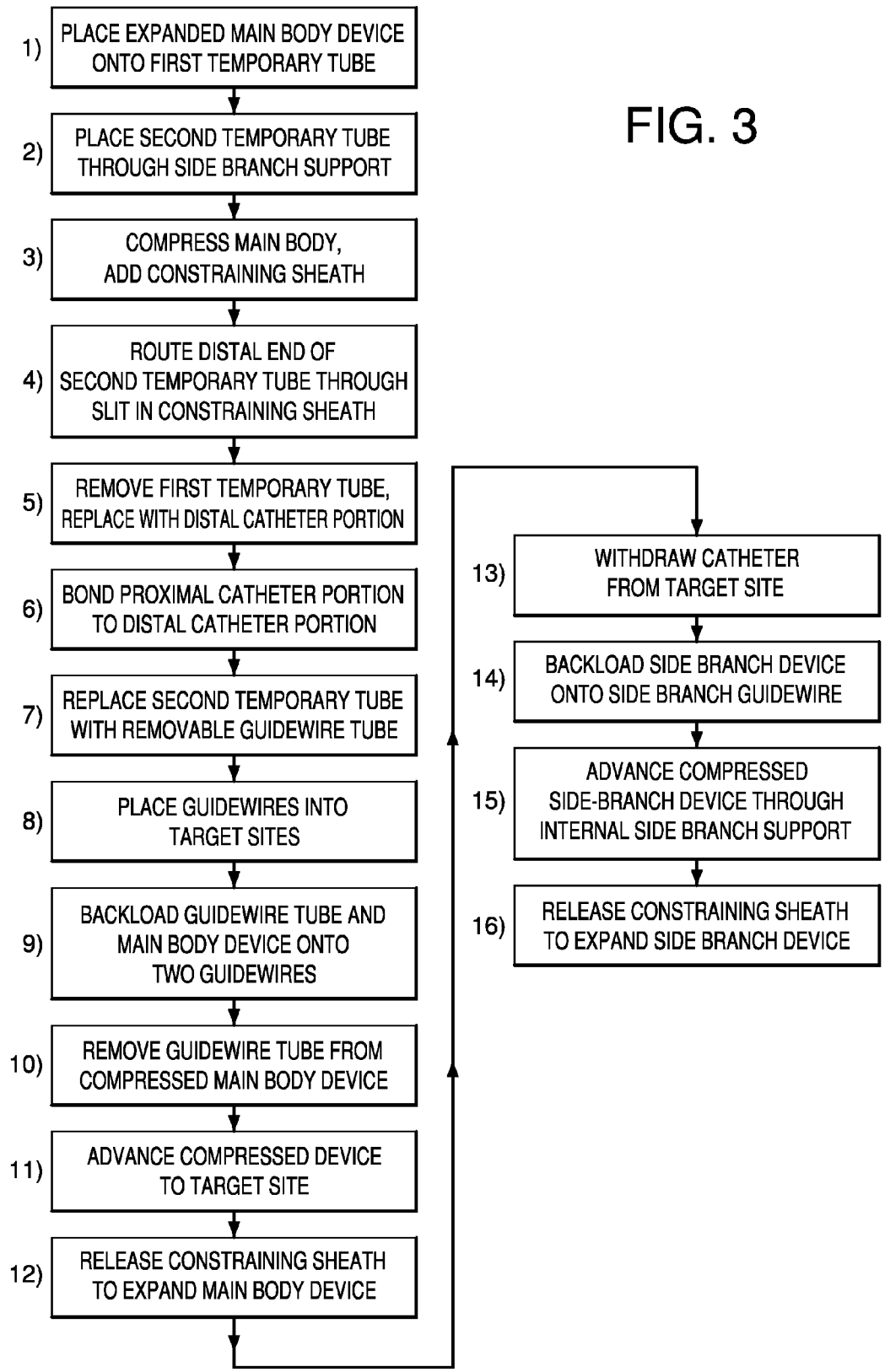
FIG. 3 is a flow chart listing the process steps used for the fabrication and delivery of a catheter assembly having a removable side branch guidewire tube.

FIG. 3 is a flow chart depicting the assembly and delivery sequence of a catheter system having a removable guidewire tube. Following are details relating to the steps listed on flowchart FIG. 3:

Step 1) Place Expanded Main-Body Device onto First Temporary Tube.

Figure 4:
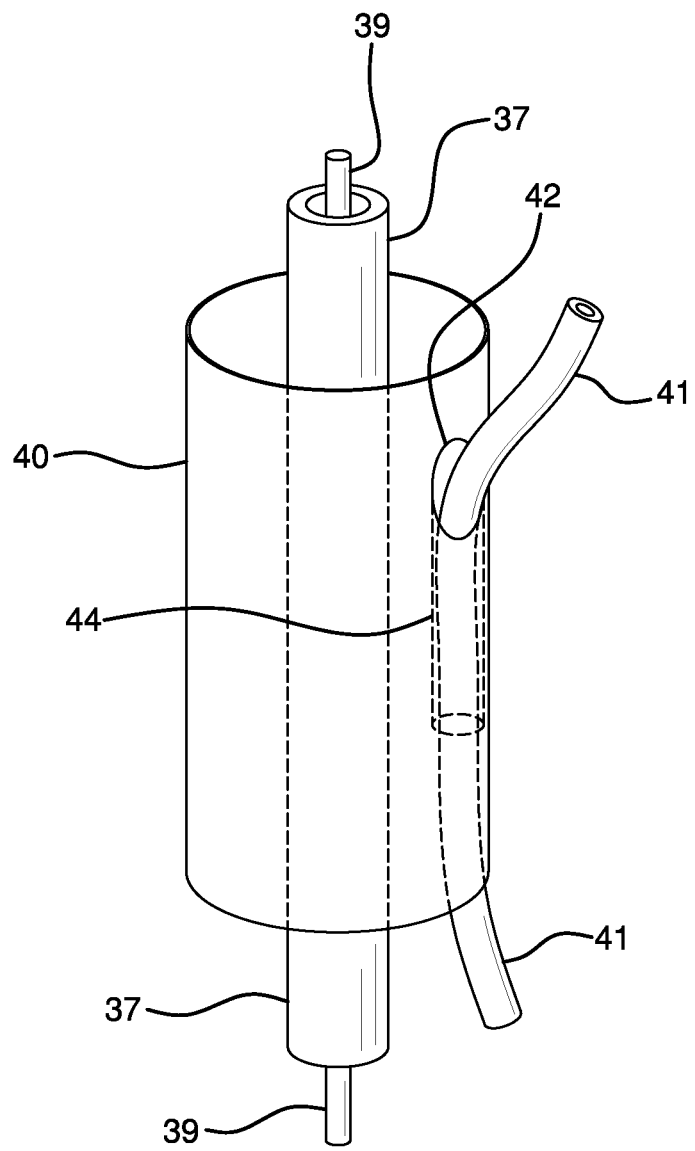
FIG. 4 is a perspective view of an expanded main body device with first temporary tube routed through the main body lumen and a second temporary tube routed through a side branch support.

Shown in FIG. 4 is an expanded main body stent graft 40 having a side wall opening 42 and an internal side branch support channel 44. A first temporary tube 37 can be inserted through the stent graft main body lumen. A first stiffening mandrel 39 can be positioned within the first temporary tube. The stent graft can be fabricated, for example, according to the methods and materials as generally disclosed in U.S. Pat. Nos. 6,042,605; 6,361,637; and 6,520,986 all to Martin et al. Details relating to exemplary fabrication and materials used for internal side branch support channel 44 can be found in U.S. Pat. No. 6,645,242 to Quinn.

Step 2) Place Second Temporary Tube Through Side Branch Support.

Referring to FIG. 4, a second temporary tube 41 can be routed through the side wall opening 42 and through the internal side branch support channel 44 to the second open end 2 of stent 40.

Step 3) Compress Main Body, Add Constraining Sheath

Figure 5B:
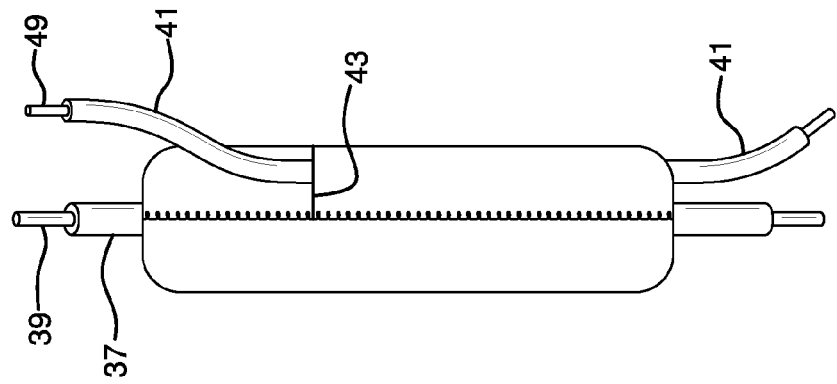
FIGS. 5A and 5B are perspective views of a compressed and constrained main body device displaying the routing of two temporary tubes.
Figure 5A:
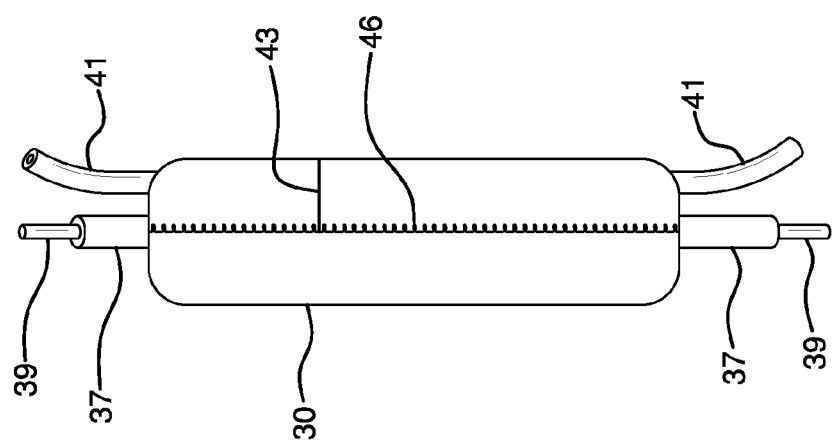

Referring to FIG. 5A, the main body stent can be compressed and held in the compressed state by a constraining sheath 30. The sheath can be laced together by a deployment cord 46. The sheath lacing forms a generally longitudinal seam along the constraining sheath. The constraining sheath can be provided with a slit 43 that is oriented perpendicular to the longitudinal seam 46. The slit can subsequently provide an exit point for the second temporary tube 41. Additionally, the second temporary tube 41 could exit through the stitch line. Details relating to constraining sheath materials, sheath methods of manufacture and main body compression techniques can be found in, for example, U.S. Pat. No. 6,352,561 to Leopold et al., and U.S. Pat. No. 6,551,350 to Thornton et al.

Step 4) Route Distal End of Second Temporary Tube Through Slit in Constraining Sheath.

As shown in FIG. 5B, the second temporary tube 41 can be routed through the slit 43. A small spring puller or hook can be inserted through the slit and used to engage the lumen of the second temporary tube. Once the lumen is engaged the second tube can be pulled through the slit as shown in FIG. 5B. After the second temporary tube 41 is routed through the constraining sheath, a second stiffening mandrel 49 can be inserted through the second temporary tube.

Step 5) Remove First Temporary Tube and Replace with Distal Catheter Portion.

Figure 6B:
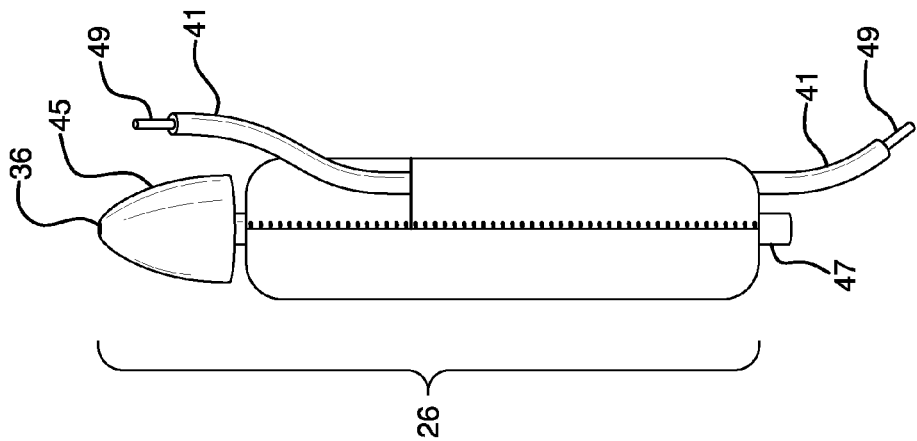
FIG. 6B is a perspective view of a main body device compressed and constrained onto a distal catheter portion.
Figure 6A:
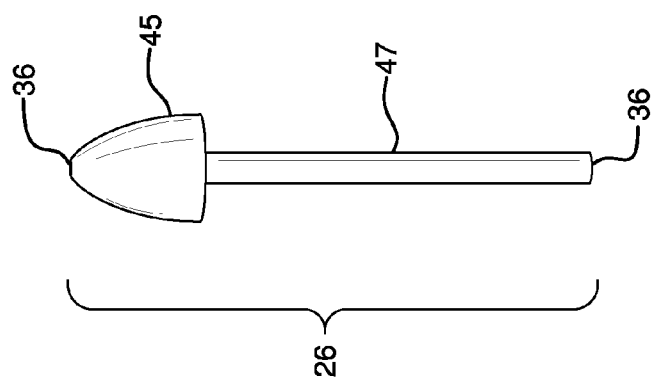
FIG. 6A is a perspective view of a distal catheter portion.

Shown in FIG. 6A is distal catheter portion 26 having a distal tip 45 and a shaft 47. The distal catheter portion 26 has a continuous lumen 36 that is sized to accommodate a guidewire. As shown in FIG. 6B, the first temporary tube can be replaced by the distal catheter portion 26. The first temporary tube 37 can be removed by placing the lumen 36 of the catheter shaft 47 onto the stiffening mandrel 39. The catheter portion 26 can then be used to push the first temporary tube out of the compressed device. After the catheter portion is fully inserted, the stiffening mandrel 39 can be removed.

Step 6) Bond Proximal Catheter Portion to Distal Catheter Portion.

Figure 7:
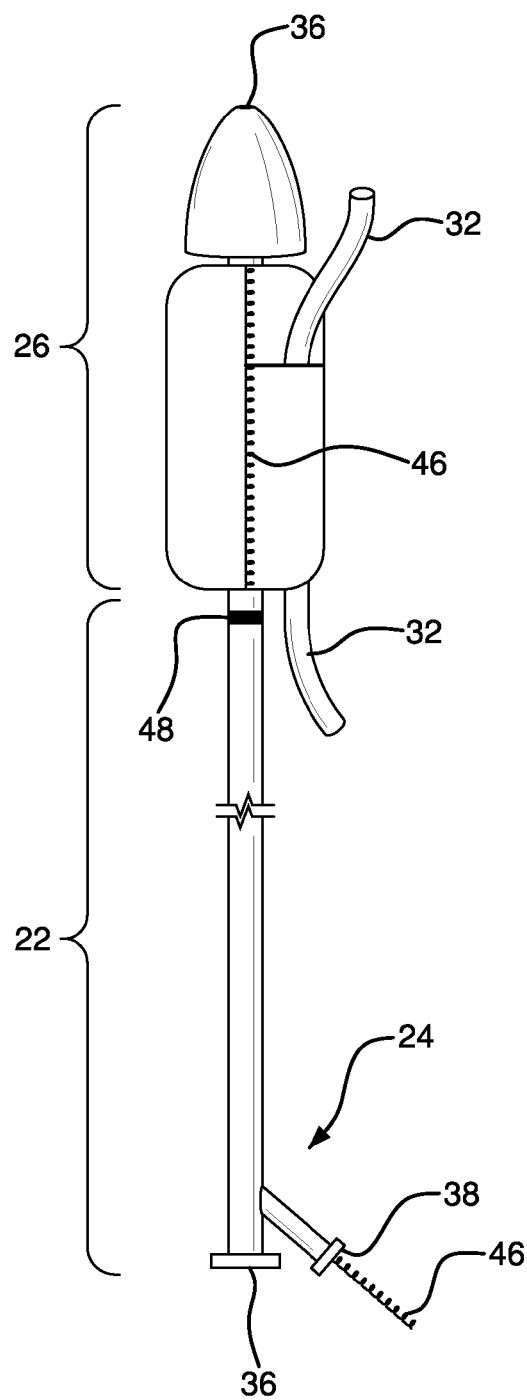
FIG. 7 is a perspective view of a compressed and constrained main body device with a proximal catheter portion bonded to a distal catheter portion.

As shown in FIG. 7, a proximal catheter portion 22 is bonded to the distal catheter portion 26 at bonding point 48. A hub assembly 24 is attached to the proximal catheter portion 22. The hub assembly 24 has a main guidewire lumen extending from distal tip 36, through the hub assembly to the proximal tip 39 of the catheter. Also shown is a deployment cord 46 routed through a deployment cord lumen 38 extending through the hub assembly 24.

The catheter and hub can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers, Pebax® polyether block amide, and metals such as stainless steels and nitinol.

The proximal and distal catheter portions can have diameters and lengths suitable for the delivery of a variety of main body stent configurations. Catheter diameters can range from about 1 mm to over 20 mm, with a preferred range of about 2 mm to about 15 mm, with a most preferred range of about 2 mm to about 6 mm. Catheter lengths can vary from about 20 cm to over 100 cm.

The removable guidewire tube can comprise the same materials listed above for the catheter and hub materials. Moreover, the tube can include a reinforcing braid material, such as metal braid.

Step 7) Replace Second Temporary Tube with Removable Guidewire Tube.

As shown in FIG. 7, the second temporary tube 41 can be replaced by a removable guidewire tube 32. The second temporary tube can be removed by placing the removable tube onto the stiffening mandrel 49. The removable tube 32 can then be pushed over the stiffening mandrel 49, driving the temporary tube out of the compressed device. After the removable guidewire tube 32 is fully inserted, the mandrel can be removed and the removable guidewire tube trimmed to length.

The guidewire tube can be fabricated from suitable medical grade materials similar to those used in the catheter materials listed in step 6) above. The guidewire tube can have inner diameters ranging from about 0.1 mm to about 2 mm, with a preferred range of about 0.2 mm to about 1.5 mm, with a most preferred range of about 0.3 mm to about 1 mm.

The guidewire tube can have a wall thickness ranging from about 0.05 mm to about 1 mm, with a preferred range of about 0.06 mm to about 0.5 mm, with a most preferred range of about 0.08 mm to about 0.3 mm.

The guidewire tube can have a length tailored for a particular stent. In general, the guidewire tube is significantly shorter than the overall catheter length and can be slightly longer than the main body stent. For example a guidewire tube can have a length ranging from about 1 cm to about 30 cm, with a preferred length ranging from about 2 cm to about 20 cm, with a most preferred length ranging from about 4 cm to about 15 cm.

Step 8) Place Guidewires into Target Sites

Figure 8:
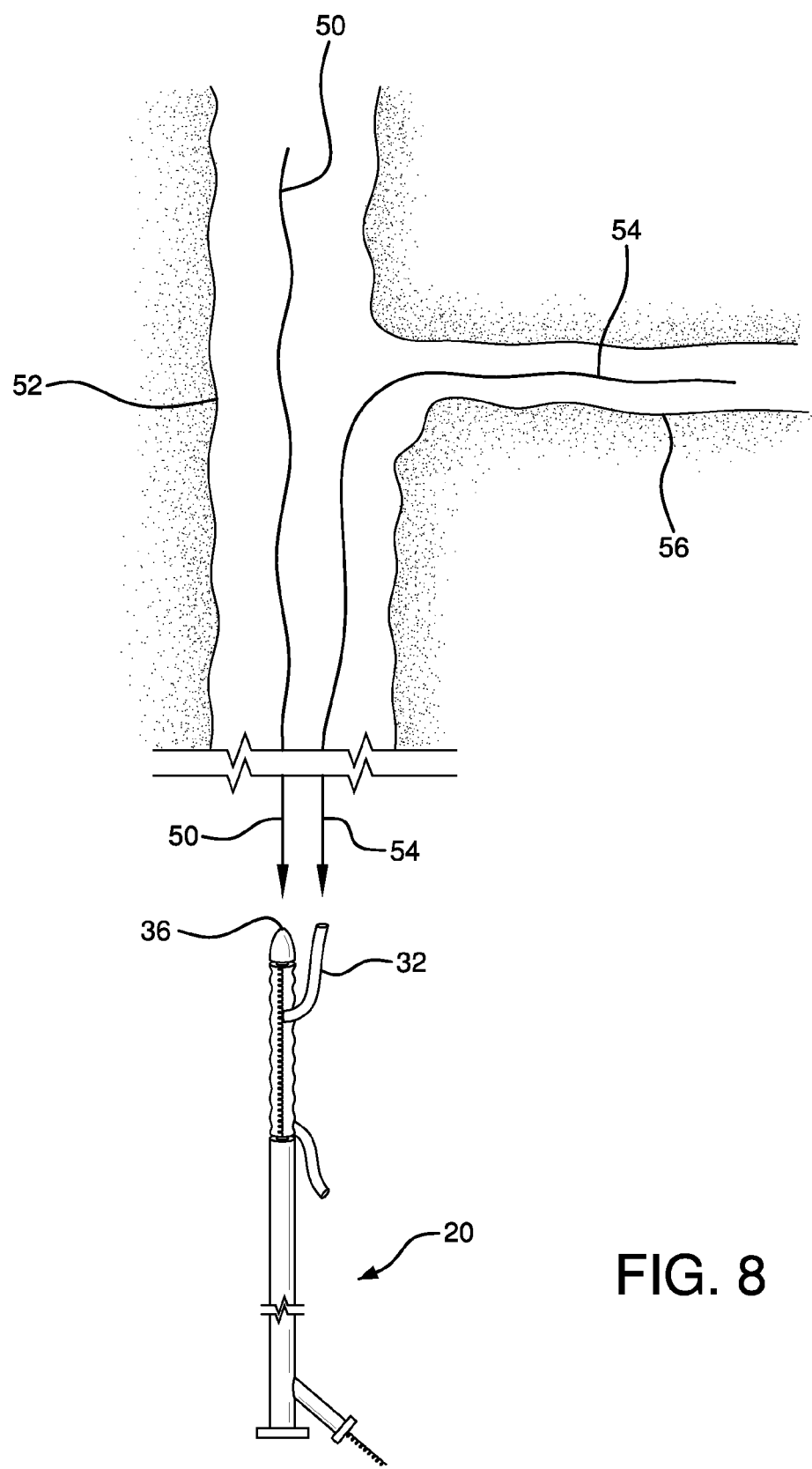
FIG. 8 is a schematic diagram showing pre-placed guidewires loaded through a compressed device with a removable guidewire tube.

As shown in FIG. 8, two guidewires can be placed into native vessels. Shown are a main body guidewire 50 placed into a main vessel 52 and a side branch guidewire 54 placed into a side branch vessel 56. An introducer sheath (not shown) can be used during the guidewire placement. A hemostatic valve (not shown) is typically used to control back-bleeding during the guidewire and subsequent device placement. Typical guidewires (with 0.035" and 0.014" diameters) can be used.

Step 9) Backload Guidewire Tube and Main Body Device onto Two Guidewires.

Figure 9:
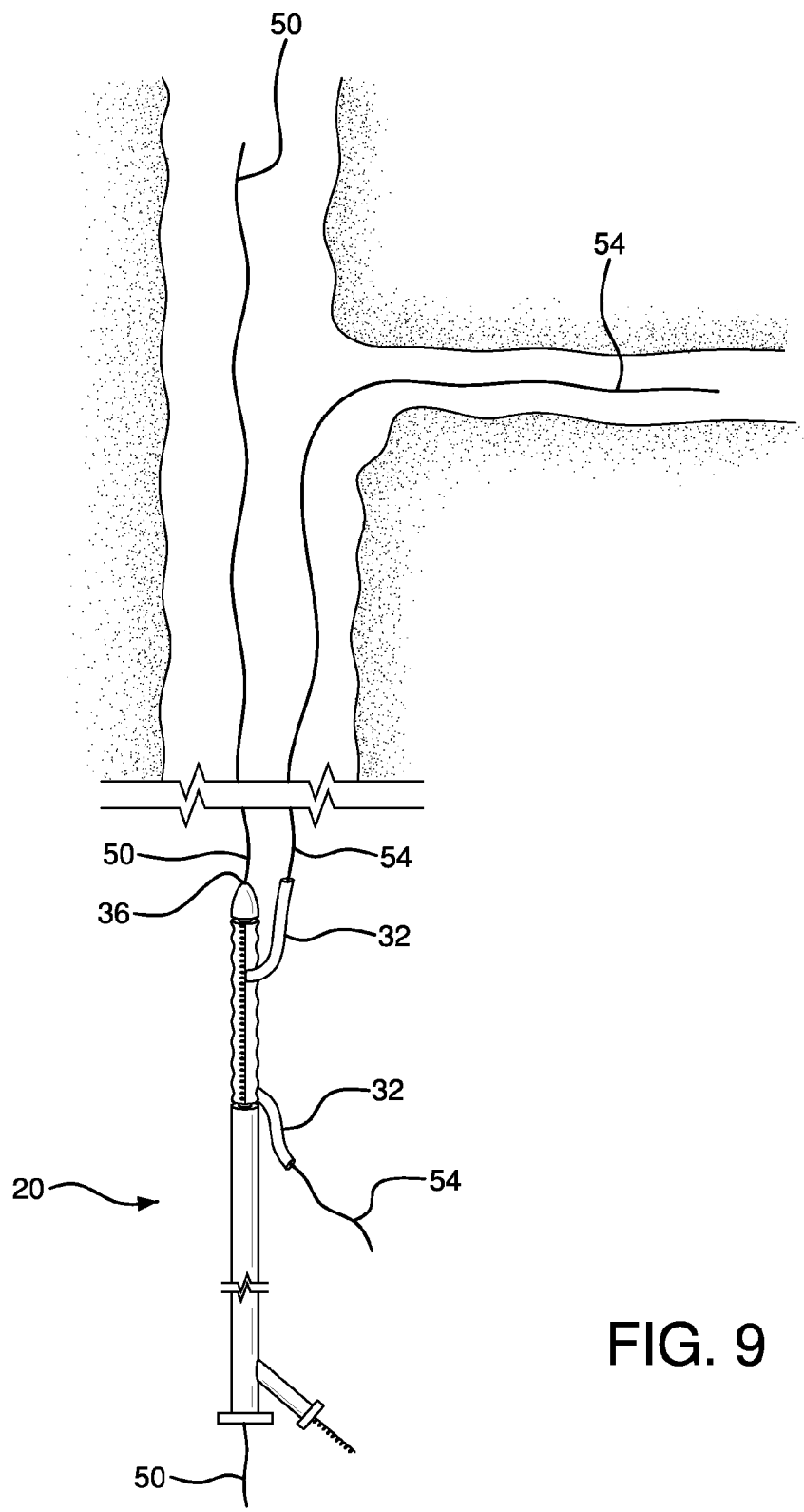
FIG. 9 is a schematic diagram showing a side branch guidewire routed through a removable guidewire tube.

As further shown in FIG. 9, the catheter assembly 20 can be back loaded onto the two guidewires. The main body guidewire 50 is threaded into the catheter main guidewire lumen 36, while the side branch guidewire 54 is threaded into the removable guidewire tube 32.

The guidewires are fully inserted through the catheter main body lumen 36 and through the removable guidewire tube 32, as depicted in FIG. 9. Shown is a main body guidewire 50 fully inserted through the catheter main guidewire lumen 36 and a side branch guidewire 54 fully inserted through the removable guidewire tube 32.

Step 10) Remove Guidewire Tube from Compressed Main Body Device

Figure 10:
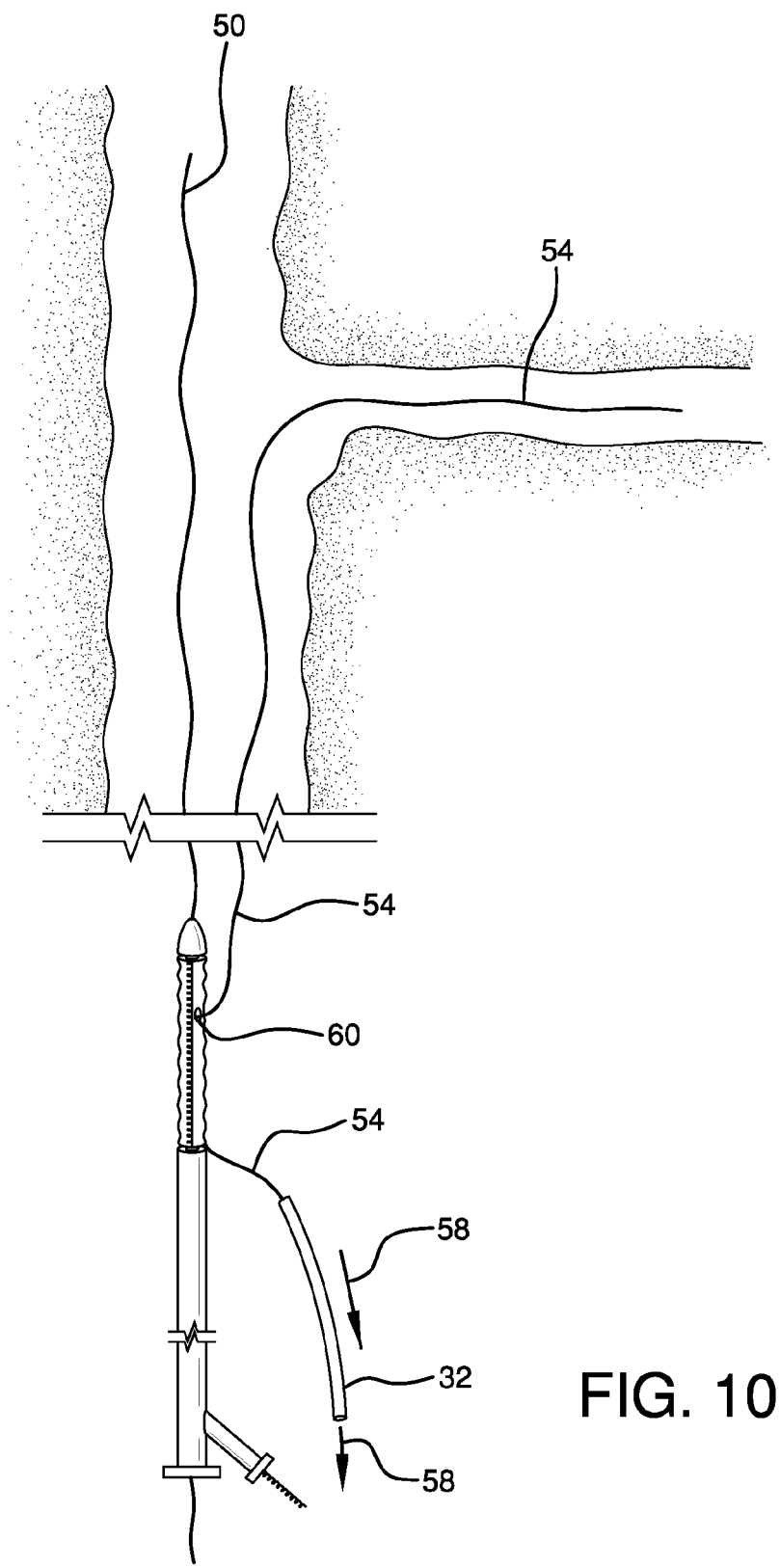
FIG. 10 illustrates the removal of a side branch guidewire tube.

As shown in FIG. 10, the guidewire tube 32 can now be removed from the catheter assembly by withdrawing the guidewire tube 32 in the direction shown by arrows 58. After removal of the guidewire tube 32, a sheath aperture 60 remains, from which the side branch guidewire 54 exits. Any suitable material may be used to fabricate the guidewire tube 32. Examples of such materials include, conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers and metals such as stainless steels and nitinol. In an aspect of the invention the material is sufficiently translucent so that the guidewire can be visualized by the practitioner as the guidewire is advanced through the guidewire tube 32. In a further aspect of the invention the end of the guidewire tube 32 that extends out the second end of the main body device is closed, or plugged. Thus, when the guidewire is inserted into the guidewire tube 32 and advanced toward the second end of the main body device the guidewire will contact the closed end of the guidewire tube. Further advancement of the guidewire can cause the guidewire tube 32 to advance beyond the second end of the main body device where it can be removed by hand. Moreover, to prevent the guidewire tube from being inserted into an introducer sheath during a procedure, the proximal end of the tube can be provided with an enlarged portion (such as a flag, knob, large diameter plug, expanded tube end, etc.) that is incapable of fitting inside the lumen of an introducer sheath.

Step 11) Advance Compressed Device to Target Site

Figure 11:
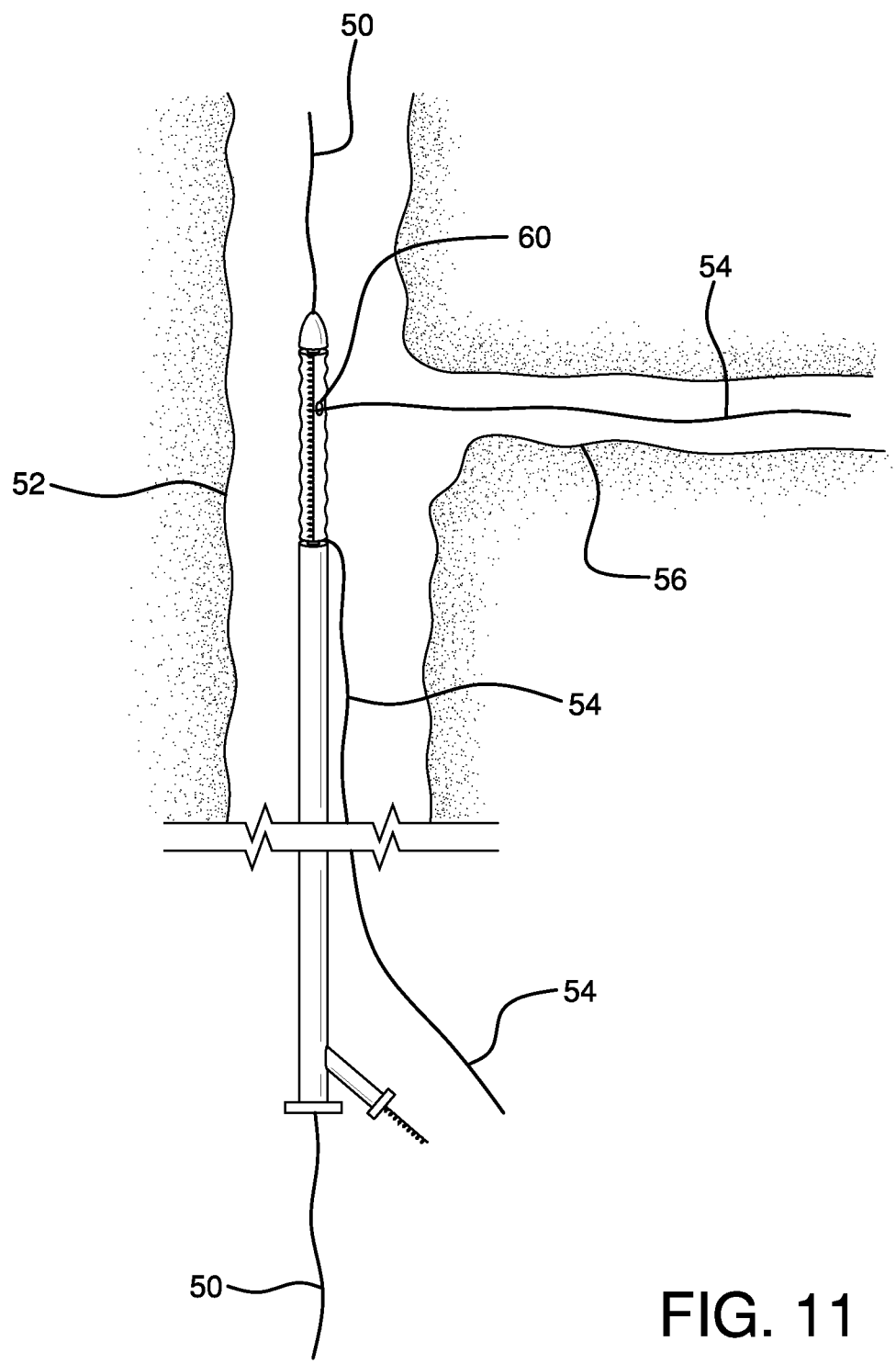
FIG. 11 is a schematic diagram showing a compressed main body device positioned at a branch vessel target site.

The catheter assembly can now be advanced to the target site. As shown in FIG. 11 the catheter and compressed main body device are advanced along the two guidewires 50, 54 until the sheath aperture 60 is aligned to the side branch vessel 56.

Step 12) Release Constraining Sheath to Expand Main Body Device

Figure 12:
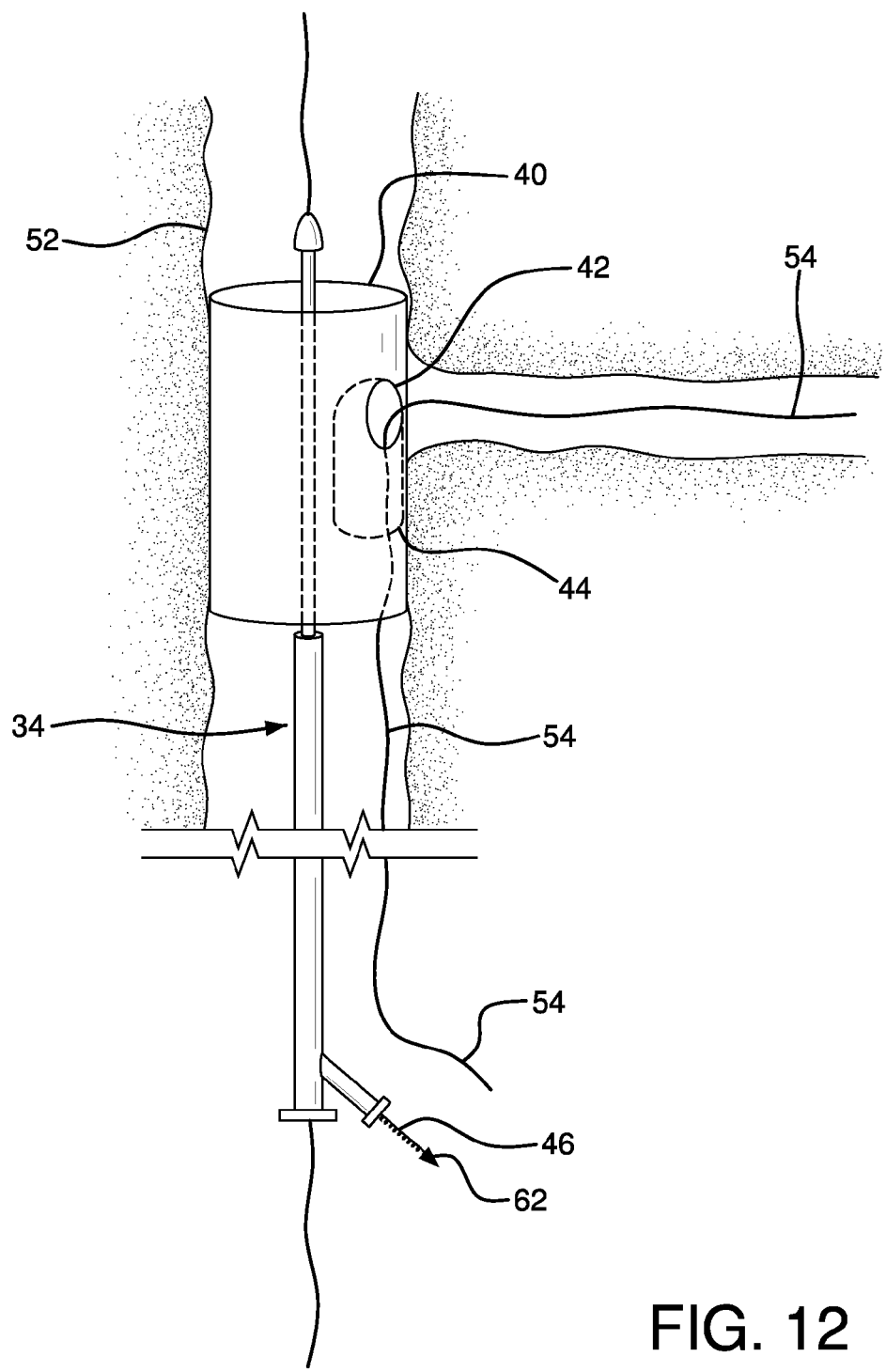
FIG. 12 is a perspective view of an expanded main body device having a side branch opening aligned to a side branch vessel.

As shown in FIG. 12, the deployment cord 46 is pulled in the direction shown by arrow 62. By pulling on the deployment cord 46 the constraining sheath is split allowing the main body device 40 to self-expand and engage the main vessel 52. The constraining sheath (not shown) can be left in-vivo since the sheath will be captured between the main body stent and the main vessel lumen. The side branch guidewire remains routed through the main body side wall opening 42, through the internal side branch support 44 and out through the proximal end of the main body device.

Step 13) Withdraw Catheter from Target Site

The catheter 34 of FIG. 12 can now be removed, leaving the expanded main body device 40 and the side branch guidewire 54 in place.

Step 14) Backload Side Branch Device onto Side Branch Guidewire.

Figure 13:
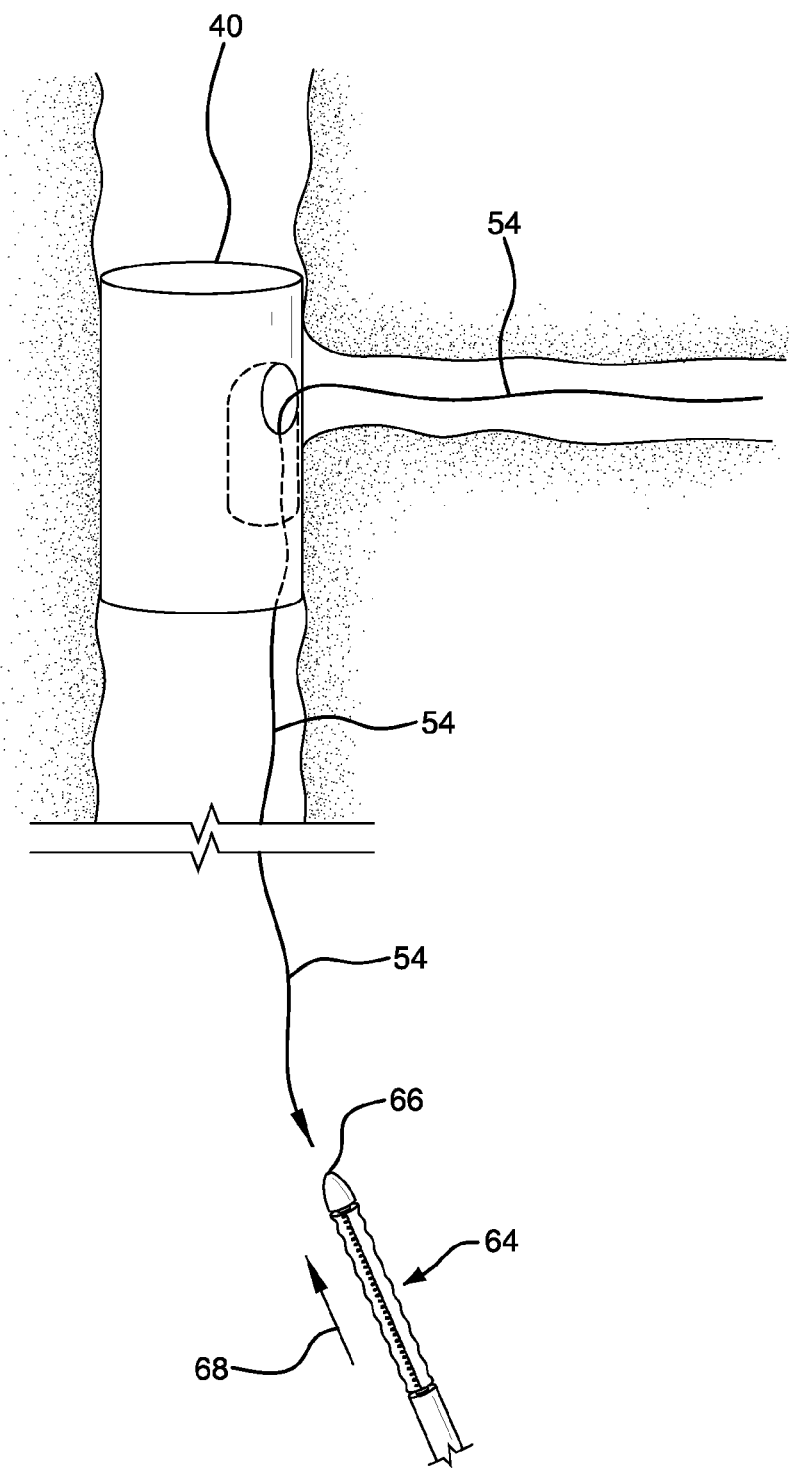
FIG. 13 illustrates the initial advancement of a compressed side branch device.

A compressed side branch stent graft can then be back loaded onto the side branch guidewire. As shown in FIG. 13, the side branch guidewire 54 can be inserted into a side branch guidewire lumen 66. The compressed side branch device 64 can then be advanced in the direction indicated by arrow 68. The compressed side branch device can be a stent or stent graft and can be constructed similar to the main body device 40, discussed above.

Figure 14:
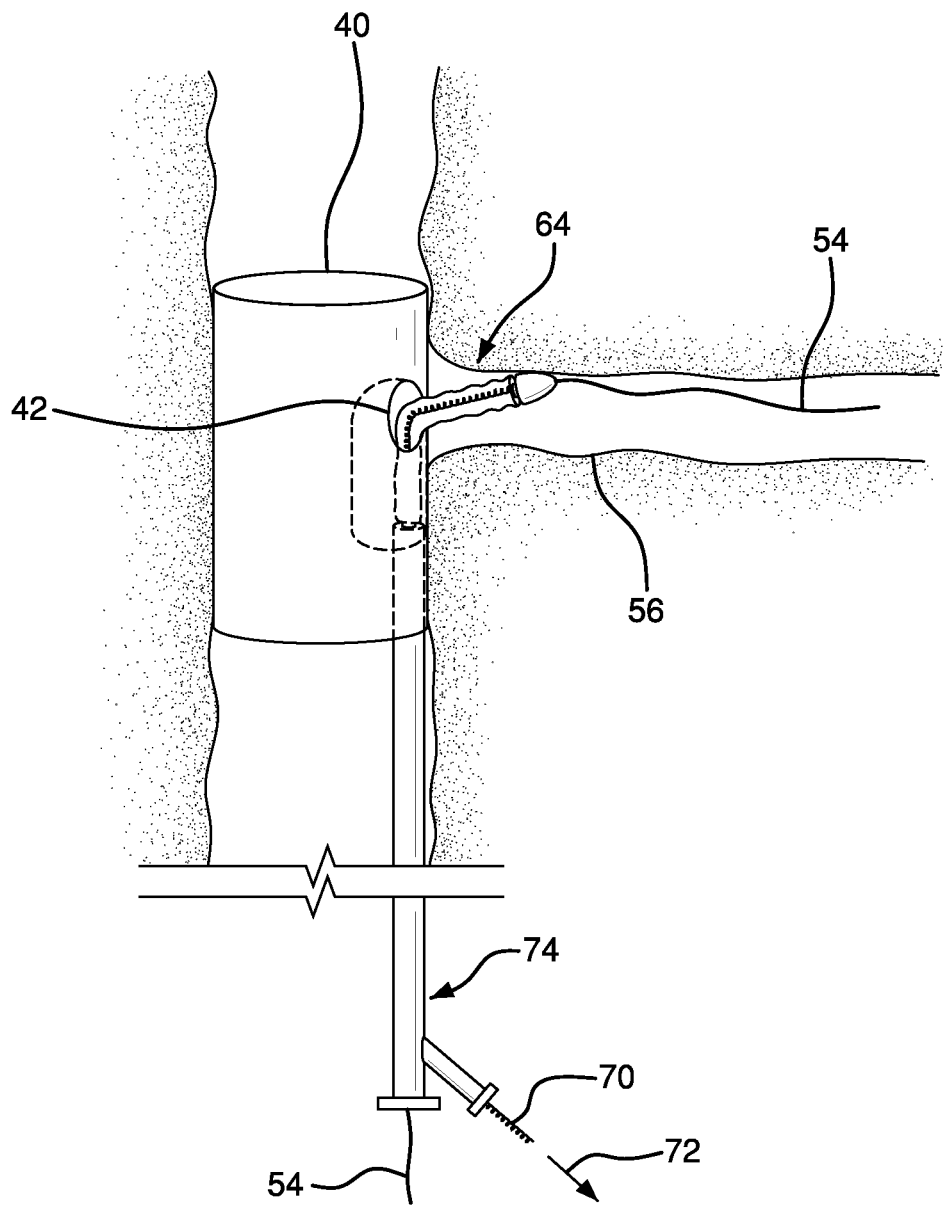
FIG. 14 shows a compressed side branch device routed through the main body device and into the side branch vessel.

Step 15) Advance Compressed Side Branch Device Through Internal Side Branch Support Channel As shown in FIG. 14, the compressed side branch device 64 can be fully advanced along guidewire 54 so that the compressed device exits the main body side wall opening 42 and enters the side branch vessel 56.

Step 16) Release Constraining Sheath to Expand Side Branch Device

Figure 15:
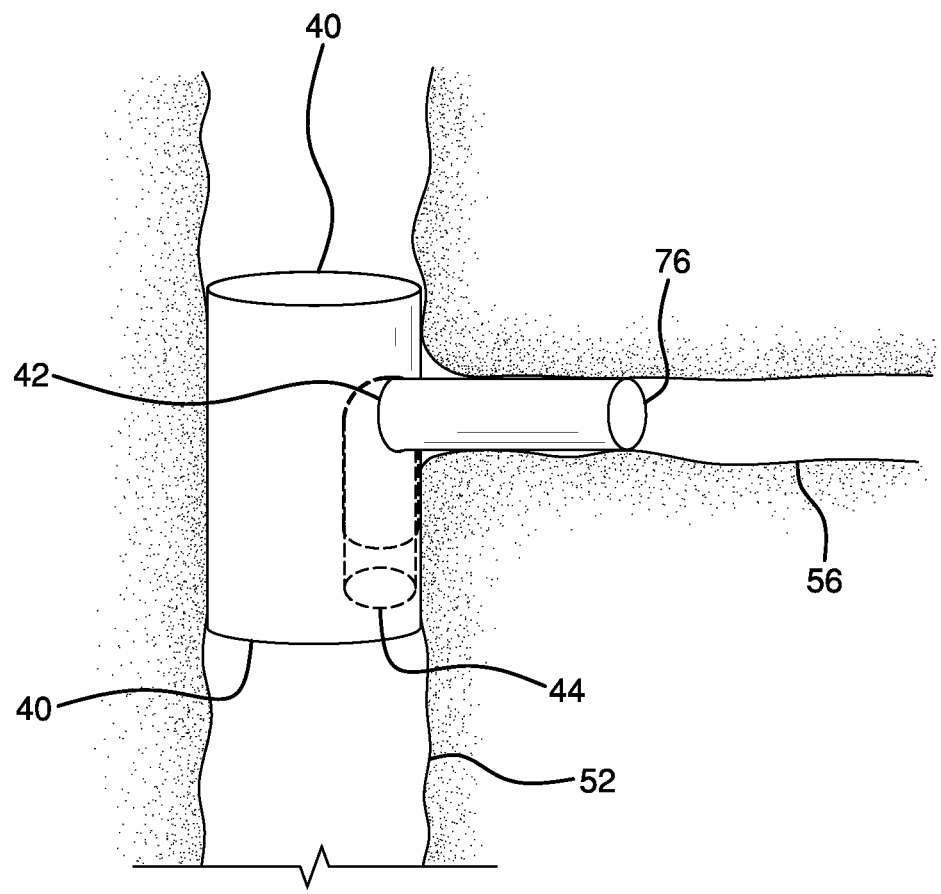
FIG. 15 is a perspective view of a fully deployed main body stent graft and a fully deployed side branch stent graft.

Referring to FIG. 14, the side branch constraining sheath can be released by pulling on the deployment cord 70 along the direction indicated by arrow 72. As shown in FIG. 15, the release of the constraining sheath allows the side branch device 76 to self-expand and engage the side branch vessel 56, the main body side wall opening 42 and the internal side-branch support channel 44. The side branch catheter can be removed after the side branch device is fully expanded. The constraining sheath (not shown) can be left in-vivo since the sheath will be captured in a fashion similar to that of the previous main body device.

The expandable prosthesis of the invention can be delivered to, for example, the aortic arch branches (arteries of the head, arms, and hands), lower branches of the aorta (celiac), renals, mesenterics, iliacs, the femoral, and lower extremities (legs, feet).

Example 1

An expandable prosthetic device having a removable guidewire tube can be fabricated as follows:

1) A self-expanding, main body stent graft can be provided having an outer diameter of 3.1 cm, a length of 15 cm and a graft wall thickness of about 0.005". The graft material can comprise ePTFE and FEP and be formed from an extruded and expanded thin walled tube that is subsequently wrapped with ePTFE film. A nitinol wire having a diameter of about 0.0165" can be helically wound to form a stent having an undulating, sinusoidal pattern. The formed, heat-treated stent can be placed onto the base graft. An additional film layer of ePTFE and FEP can be wrapped onto the stent and base graft to selectively adhere the stent to the graft.

2) The main body stent graft can have an internal side-branch support channel formed into the graft wall. Details relating to exemplary fabrication and materials used for an internal side branch support channel can be found in U.S. Pat. No. 6,645,242 to Quinn.

3) A failsafe feature to prevent the inadvertent "non-removal" of the guidewire tube can be incorporated into the guidewire tube. A distal portion of a removable guidewire tube can be formed from an 18 cm length of Pebax® 5533 tubing having a 304 stainless steel braid (0.00075"×0.003") and a polyimide inner lumen lining (from Phelps Dodge).

The tube can have an outer diameter of 0.0455" and an inner diameter of 0.039". A proximal section of transparent tubing (Pebax®7233, OD of 0.057", ID of 0.047", from Specialized Engineering) can be cut to a length of about 4 cm.

A 0.038" mandrel can be inserted into the first distal tube. The transparent proximal tube section can be placed over the mandrel so that the transparent tube overlaps the first distal tube by about 1 cm. A 2 cm long section of 0.060" ID FEP shrink tubing can be placed onto the overlapped tube sections. Using a narrow hot box (set at 420° F.), the tube overlap can be heated until the tubes reflow and bond together. A spherical bead of UV curable adhesive can be applied to the end of the transparent tubing and cured to form a plug.

When a side branch guidewire is subsequently loaded into the guidewire tube, the transparent proximal section provides visual feedback that the guidewire has advanced through and fully exited the stent graft. The adhesive plug effectively blocks further guidewire advancement; therefore the stent device cannot be further advanced without removing the guidewire tube. This failsafe prevents the inadvertent "non-removal" of the guidewire tube.

4) A temporary polymeric tube (such as a PTFE tube) can be threaded through the main body stent, through the internal side branch support and out through the main body side wall opening as shown, for example, in FIG. 4. This temporary tube can be replaced with the removable guidewire tube after compression of the device. The stent device can then be compressed using temporary tethers and a tapered pull-through compression die. The main body stent can be compressed onto a temporary mandrel having a 0.066" OD and maintained in the compressed state by a removable constraining sheath. The temporary tube can be removed and the compressed device transferred onto a distal catheter portion (as shown, for example, in FIG. 6A, item 26). The distal catheter portion can have a shaft OD of 0.068".

5) A proximal catheter portion (as shown, for example, in FIG. 7, 22) can be bonded onto the proximal end of the distal catheter portion (as shown, for example, in FIG. 7, 26). A unitary hub assembly (FIG. 7, 24) can be bonded to the proximal end of the proximal catheter portion (as shown in, for example, FIG. 7, 22) to complete assembly. The deployment cord can be appropriately routed through the proximal catheter and hub assembly.

What is claimed:

1. An apparatus for treating a vessel comprising:
   an expandable stent graft having a main lumen and a side wall opening;
   a constraining sheath configured to compress and hold the expandable stent graft in a compressed state, wherein the constraining sheath comprises a slit aligned with the side wall opening, the slit is perpendicular to a seam; and
   a deployment cord configured to hold together the constraining sheath and form the seam along a longitudinal axis of the constraining sheath and open the constraining sheath along the seam to allow the expandable stent graft to expand in response to displacement of the deployment cord.

2. The apparatus of claim 1, wherein the expandable stent graft further comprises an internal side branch support channel aligned with the side wall opening.

3. The apparatus of claim 1, wherein the constraining sheath constrains the expandable stent graft in the compressed state for delivery within the vessel.

4. The apparatus of claim 1, wherein the constraining sheath is configured to remain with the expandable stent graft after expansion of the expandable stent graft.

5. The apparatus of claim 1, wherein the expandable stent graft comprises a self-expanding stent.

6. The apparatus 5, wherein the self-expanding stent comprises nitinol.

7. The apparatus 1, wherein the expandable stent graft includes a graft, the graft comprises a material selected from the group consisting of ePTFE, nylon, polyester, polyethylene, polypropylene, polytetrafluoroethylene, polyurethane and elastomeric organosilicon polymers.

8. The apparatus 1, wherein the expandable stent graft is balloon expandable.

9. The apparatus of claim 1, wherein the side wall opening and the slit are sized to accommodate a removable guidewire tube.

10. The apparatus of claim 1, wherein the side wall opening and the slit are sized to accommodate a side branch device.

* * * * *